(12) United States Patent
Miike et al.

(10) Patent No.: US 12,023,005 B2
(45) Date of Patent: Jul. 2, 2024

(54) POSITIONING A TUBE IN A LUMEN VIA TRANSILLUMINATION

(71) Applicants: Acera LLC, Beverly, MA (US); Neuroceuticals Inc., Tokyo (JP); Fraen Corporation, Reading, MA (US)

(72) Inventors: Shinya Miike, Tokyo (JP); Thomas V. Root, Beverly, MA (US); Michael S. Epstein, Saint Michaels, MD (US); Michael Cook, Salem, MA (US); Carlton Jones, Boxford, MA (US)

(73) Assignees: Fraen Corporation, Reading, MA (US); Neuroceuticals Inc., Tokyo (JP); Acera LLC, Beverly, MA (US)

( * ) Notice: Subject to any disclaimer, the term of this patent is extended or adjusted under 35 U.S.C. 154(b) by 573 days.

(21) Appl. No.: 16/731,852

(22) Filed: Dec. 31, 2019

(65) Prior Publication Data
US 2020/0205640 A1 Jul. 2, 2020

Related U.S. Application Data

(60) Provisional application No. 62/787,688, filed on Jan. 2, 2019.

(51) Int. Cl.
*A61B 1/00* (2006.01)
*A61B 5/00* (2006.01)
(Continued)

(52) U.S. Cl.
CPC .......... *A61B 1/0017* (2013.01); *A61B 5/0059* (2013.01); *A61B 5/06* (2013.01);
(Continued)

(58) Field of Classification Search
CPC ....... A61B 1/0017; A61B 5/0059; A61B 5/06; A61B 5/061; A61J 15/0003;
(Continued)

(56) References Cited

U.S. PATENT DOCUMENTS 2,908,197 A 10/1959 Wells et al.
3,285,242 A 11/1966 Wallace
(Continued)

FOREIGN PATENT DOCUMENTS

CN 201680208 U 12/2010
CN 205079073 U 3/2016
(Continued)

OTHER PUBLICATIONS

Japanese Office Action, JP2018-542993, dated May 12, 2021, 15 pages.
(Continued)

*Primary Examiner* — Tri T Ton

(74) *Attorney, Agent, or Firm* — Potomac Law Group, PLLC; Reza Mollaaghababa; Brian Hairston

(57) ABSTRACT

An illumination system for illuminating a lumen within a body of a patient comprising a tube having a proximal end and an opposed distal end and an internal chamber, the tube being configured for placement within a lumen of the body. The system also includes an illumination subsystem including an optical fiber that is sized and configured to seat within the internal chamber of the tube and a light source for generating light that is emitted by the fiber optic cable. The optical fiber, when mounted within the tube and when the light source generates light, emits light at the distal end of the tube so as to transilluminate the lumen and surrounding tissue so as to be able to locate the distal end of the tube within the lumen of the patient.

21 Claims, 21 Drawing Sheets

(51) Int. Cl.
*A61B 5/06* (2006.01)
*A61J 15/00* (2006.01)
*A61M 25/00* (2006.01)
*F21V 23/06* (2006.01)
*G02B 23/24* (2006.01)
*F21Y 115/10* (2016.01)

(52) U.S. Cl.
CPC ........... *A61B 5/061* (2013.01); *A61J 15/0003* (2013.01); *A61M 25/003* (2013.01); *F21V 23/06* (2013.01); *G02B 23/2469* (2013.01); *F21Y 2115/10* (2016.08)

(58) Field of Classification Search
CPC ... A61M 25/003; F21V 23/06; F21Y 2115/10; G02B 23/2469
USPC ......................................................... 604/21
See application file for complete search history.

(56) References Cited

U.S. PATENT DOCUMENTS

| | | | |
|---|---|---|---|
| 3,592,199 | A | 7/1971 | Ostensen |
| 4,414,608 | A | 11/1983 | Furihata |
| 4,726,074 | A | 2/1988 | Baclit et al. |
| D331,634 | S | 12/1992 | Browne |
| 5,353,208 | A | 10/1994 | Moore |
| 5,609,561 | A | 3/1997 | Uehara et al. |
| 5,682,199 | A | 10/1997 | Lankford |
| 5,702,349 | A | 12/1997 | Morizumi |
| 5,743,848 | A | 4/1998 | Koeda et al. |
| 5,765,223 | A | 6/1998 | McCausland |
| 6,007,485 | A | 12/1999 | Koeda et al. |
| 6,099,147 | A | 8/2000 | Ziegenfuss |
| 6,135,947 | A | 10/2000 | Watanabe et al. |
| 6,257,741 | B1 | 7/2001 | Williams et al. |
| 6,540,389 | B1 | 4/2003 | Novak et al. |
| 6,819,505 | B1 | 11/2004 | Cassarly et al. |
| 6,937,791 | B2 | 8/2005 | Guy |
| 6,991,603 | B2 | 1/2006 | Krupa et al. |
| 7,115,091 | B2 | 10/2006 | Root et al. |
| D533,939 | S | 12/2006 | Root et al. |
| 7,193,519 | B2 | 3/2007 | Root et al. |
| 7,198,397 | B2 | 4/2007 | Bennett et al. |
| 7,229,201 | B2 | 6/2007 | Krupa et al. |
| D551,762 | S | 9/2007 | Root et al. |
| D561,336 | S | 2/2008 | Laflash et al. |
| D581,052 | S | 11/2008 | Root et al. |
| D623,786 | S | 9/2010 | Wessel |
| 7,798,692 | B2 | 9/2010 | Krupa et al. |
| D629,537 | S | 12/2010 | Hsu et al. |
| D631,567 | S | 1/2011 | Lodhie |
| 8,033,704 | B2 | 10/2011 | Krupa et al. |
| 8,152,715 | B2 | 4/2012 | Root et al. |
| D662,231 | S | 6/2012 | Sakamoto et al. |
| D663,445 | S | 7/2012 | Sakamoto et al. |
| D663,464 | S | 7/2012 | Lee |
| D666,340 | S | 8/2012 | Sakamoto et al. |
| D669,200 | S | 10/2012 | Chen et al. |
| D671,241 | S | 11/2012 | Sakamoto et al. |
| D671,242 | S | 11/2012 | Sakamoto et al. |
| D671,243 | S | 11/2012 | Sakamoto et al. |
| D675,349 | S | 1/2013 | Parker et al. |
| D685,506 | S | 7/2013 | Pickard et al. |
| D690,383 | S | 9/2013 | Sheikh et al. |
| 8,534,890 | B2 | 9/2013 | Goto et al. |
| 8,801,253 | B2 | 8/2014 | Krupa et al. |
| D715,463 | S | 10/2014 | Jun |
| 9,022,628 | B2 | 5/2015 | Krupa et al. |
| 9,055,863 | B2 | 6/2015 | Krupa et al. |
| D739,586 | S | 9/2015 | Hong |
| D744,674 | S | 12/2015 | Wu et al. |
| D753,322 | S | 4/2016 | Taylor |
| D760,928 | S | 7/2016 | Bao |
| D768,321 | S | 10/2016 | Inskeep |
| D775,752 | S | 1/2017 | Nook et al. |
| D778,473 | S | 2/2017 | Cooper |
| D793,595 | S | 8/2017 | Lesperance et al. |
| D804,064 | S | 11/2017 | Taylor et al. |
| D810,325 | S | 2/2018 | Guo |
| D813,424 | S | 3/2018 | Shum et al. |
| D836,227 | S | 12/2018 | Root |
| 10,281,709 | B2 | 5/2019 | Root et al. |
| 10,768,407 | B2 | 9/2020 | Root et al. |
| 10,782,518 | B2 | 9/2020 | Root et al. |
| 11,016,282 | B2 | 5/2021 | Root et al. |
| 2003/0009084 | A1 | 1/2003 | May et al. |
| 2003/0074708 | A1 | 4/2003 | Hogg |
| 2003/0091820 | A1 | 5/2003 | Robbins |
| 2003/0158503 | A1 | 8/2003 | Matsumoto |
| 2004/0213001 | A1 | 10/2004 | Sayers et al. |
| 2004/0218858 | A1 | 11/2004 | Guy |
| 2004/0246744 | A1 | 12/2004 | Krupa et al. |
| 2005/0162848 | A1 | 7/2005 | Dalton et al. |
| 2005/0201100 | A1 | 9/2005 | Cassarly et al. |
| 2006/0183977 | A1 | 8/2006 | Ishigami et al. |
| 2007/0104664 | A1 | 5/2007 | Maltezos et al. |
| 2007/0173695 | A1 | 7/2007 | Hirata |
| 2007/0253188 | A1 | 11/2007 | Klipstein et al. |
| 2008/0027408 | A1 | 1/2008 | Wilson et al. |
| 2008/0039715 | A1* | 2/2008 | Wilson ............... A61B 5/06 600/424 |
| 2008/0091064 | A1 | 4/2008 | Laser |
| 2008/0174996 | A1 | 7/2008 | Lu et al. |
| 2008/0194973 | A1* | 8/2008 | Imam ............... A61B 90/39 600/478 |
| 2009/0040783 | A1 | 2/2009 | Krupa et al. |
| 2009/0185392 | A1 | 7/2009 | Krupa |
| 2009/0287197 | A1 | 11/2009 | Hanley et al. |
| 2010/0226127 | A1 | 9/2010 | Bigliatti et al. |
| 2010/0277894 | A1 | 11/2010 | Kim |
| 2011/0194295 | A1 | 8/2011 | Householder et al. |
| 2012/0184924 | A1 | 7/2012 | Ejike et al. |
| 2013/0046172 | A1* | 2/2013 | Waitzman ............... A61B 90/30 600/424 |
| 2014/0148653 | A1 | 5/2014 | McMahon et al. |
| 2014/0275986 | A1* | 9/2014 | Vertikov ............... A61B 5/0066 600/424 |
| 2015/0219313 | A1 | 8/2015 | Marcaly |
| 2016/0050990 | A1 | 2/2016 | Hayes |
| 2017/0122525 | A1 | 5/2017 | Root et al. |
| 2017/0123131 | A1 | 5/2017 | Root et al. |
| 2017/0123199 | A1 | 5/2017 | Jones et al. |
| 2017/0197002 | A1 | 7/2017 | Dobrinsky et al. |
| 2017/0274184 | A1* | 9/2017 | Isaacson ............ A61B 5/15003 |
| 2019/0361217 | A1 | 11/2019 | Root et al. |
| 2020/0081241 | A1 | 3/2020 | Root et al. |
| 2020/0205640 | A1 | 7/2020 | Miike et al. |
| 2021/0278657 | A1 | 9/2021 | Root et al. |
| 2021/0299298 | A1 | 9/2021 | Root et al. |
| 2021/0307421 | A1 | 10/2021 | Root et al. |

FOREIGN PATENT DOCUMENTS

| | | |
|---|---|---|
| EP | 2846179 A2 | 3/2015 |
| JP | S56-59005 A | 5/1981 |
| JP | H04288960 A | 10/1992 |
| JP | H0751282 A | 2/1995 |
| JP | H8-10220 A | 1/1996 |
| JP | 2000171725 A | 6/2000 |
| JP | 200240299 | 7/2000 |
| JP | 3148028 B2 | 3/2001 |
| JP | 2002345748 A | 12/2002 |
| JP | 2004536639 A | 12/2004 |
| JP | 200759073 | 8/2005 |
| JP | 200791119 A | 4/2007 |
| JP | 2008539479 A | 11/2008 |
| JP | 2010528818 A | 8/2010 |
| JP | 201325924 | 7/2011 |
| JP | 2013123477 A | 6/2013 |
| JP | 2013533049 A | 8/2013 |
| JP | 2013198644 A | 10/2013 |
| JP | 2009056290 A | 5/2014 |

(56) References Cited

FOREIGN PATENT DOCUMENTS

| | | |
|---|---|---|
| JP | 2015056137 A | 3/2015 |
| JP | 2015077336 A | 4/2015 |
| JP | 2016087091 A | 5/2016 |
| KR | 20190067110 A | 6/2019 |
| WO | 2008016895 A2 | 2/2008 |
| WO | 2008017718 A1 | 2/2008 |
| WO | 2010091097 A1 | 8/2010 |
| WO | 2015038971 A1 | 3/2015 |
| WO | 2018207753 A1 | 11/2018 |

OTHER PUBLICATIONS

European Extended Search Report, 21164168.3, dated Apr. 23, 2021, 7 pages.
European Examination Report, 16798028.3, dated Jul. 1, 2021, 4 pages.
International Preliminary Report on Patentability, PCT/US2019/069111, dated Jun. 16, 2021, 6 pages.
International Search Report and Written Opinion, PCT/US2021/025050, dated Jul. 6, 2021, 13 pages.
European Examination Report, 16794169.9, dated Nov. 17, 2021, 10 pages.
International Invitation to Pay Additional fees and Partial Search Report, PCT/US2021/022948, dated Jun. 29, 2021, 13 pages.
International Preliminary Report on Patentability, PCT/US2019/069111, dated Jul. 15, 2021, 7 pages.
International Search Report and Written Opinion, PCT/US2021/022948, dated Aug. 19, 2021, 21 pages.
Japanese Office Action, JP2018-542988, dated Sep. 1, 2021, 4 pages.
Japanese Office Action, JP2018-542988, dated Oct. 21, 2020, 10 pages.
Japanese Office Action, JP2018-542993, dated Oct. 14, 2020, 14 pages.
Merriam-Webster, https://www.merriam-webster.com/dictionary/periphery, Oct. 20, 2020, 8 pages.
Oxford English Dictionary, https://www.oed.com/view/Entry/141021#eid30851400, Oct. 20, 2020, 2 pages.
United States Examiner's Answer to Appeal Brief, U.S. Appl. No. 15/337,922, dated Oct. 23, 2020, 10 pages.
European Search Report, 16794163.2, dated Jan. 7, 2020, 7 pages.
International Preliminary Report on Patentability for corresponding PCT Application No. PCT/US2016/059361, dated May 11, 2018, 10 pages.
International Search Report and Written Opinion, PCT/US2019/069111, dated Mar. 25, 2020, 24 pages.
International Search Report/Written Opinion for corresponding PCT Application No. PCT/US2016/059361, dated Apr. 4, 2017, 16 pages.
International Search Report/Written Opinion for corresponding PCT Application No. PCT/US2016/059406, dated Apr. 7, 2017, 9 pages.
International Search Report/Written Opinion for corresponding PCT/US2016/059451, dated Jun. 19, 2017; 15 pages.
Invitation to Pay Additional Fees and, Where Applicable, Protest Fee, for PCT/US2016/059451, dated Mar. 16, 2017; 6 pages.
Invitation to Pay Additional Fees for corresponding PCT Application No. PCT/US2016/059361, dated Feb. 3, 2017, 6 pages.
Office Action (Notice of Reasons for Refusal) dated Oct. 3, 2023 for Japanese Patent Application No. 2021-538760.
Canadian Office Action for Canadian Patent Application No. 3,125,671 dated Dec. 20, 2023.
European Office Action (Communication Pursuant to Article 94(3) EPC) for European Patent Application No. 19845684.0 dated Dec. 20, 2023.

\* cited by examiner

POSITIONING A TUBE IN A LUMEN VIA TRANSILLUMINATION

RELATED APPLICATION

This patent application claims priority to U.S. provisional patent application Ser. No. 62/787,688, filed on Jan. 2, 2019, and entitled Positioning Nasogastric Tube Via Transillumination, the contents of which are herein incorporated by reference.

BACKGROUND

The present invention relates generally to a systems and method for illuminating an interior lumen within a patient, and specifically relates to illuminated tubes that can be safely guided along a patient's lumen, such as for example a gastrointestinal tract, by monitoring light emitted from a source coupled to the tube.

Each year, in the United States, about 1.2 million nasogastric tubes are placed in patients with a significant fraction of such tubes placed in pediatric patients. One example of a nasogastric tube is a nasogastric feeding tube that can be used to administer water, nourishment and/or medicine to a patient. For example, a so-called Dobbhoff feeding tube is a small-bore flexible tube that can be inserted through a patient's nose to the stomach, and from the stomach to the first part of the small intestine (duodenum). It can be made of a radiopaque polymeric material to allow its placement using an X-ray or fluoroscope. A nasogastric tube can also be employed for other purposes. For example, a nasogastric tube can be in the form of a large bore tube that can be used for a variety of different purposes, such as decompressing the stomach for surgery and to prevent nausea/vomiting.

Although placement of nasogastric tubes in patients is relatively routine, there is a risk associated with each insertion. A misplaced nasogastric tube can lead to serious and even fatal complications. One conventional method for verification of the placement of a nasogastric tube is the measurement of the acidity of the gastric aspirate. Another method is the use of radiography to verify the location of the nasogastric tube. These conventional methods, however, suffer from a number of shortcomings. For example, the measurement of acidity can result in false affirmation of the placement of the nasogastric tube. Further, the radiation exposure associated with radiography is of great concern in pediatric patients.

Accordingly, there is a need for improved nasogastric feeding devices as well as improved methods for their insertion into a patient's gastrointestinal tract.

SUMMARY OF THE INVENTION

The present invention is directed to the ability to illuminate via light an internal or interior lumen of a patient via a fiber optic cable and an attached light source such that at least a portion of the light can be externally observed, e.g., via the naked eye or a camera. The observed light can be employed to guide a diagnostic and/or therapeutic tube (e.g., a catheter) through the lumen. The interior lumen can be any suitable lumen such as a nasogastric passage, a cardiac passage and the like.

According to one practice, the present invention is directed to an illumination system for illuminating a lumen within a body of a patient, comprising a tube having a proximal end and an opposed distal end and an internal chamber, where the tube is configured for placement within a lumen of the body, and an illumination subsystem including an optical fiber that is sized and configured to seat within the internal chamber of the tube and a light source for generating light that is emitted by the fiber optic cable. The optical fiber, when mounted within the tube and when the light source generates light, emits light at the distal end of the tube so as to transilluminate the lumen and surrounding tissue so as to be able to locate (e.g., visually or with an external device such as a camera) the distal end of the tube within the lumen of the patient.

The tube has at least one opening formed in a wall thereof, and the optical fiber has a proximal end configured for receiving light from the light source and a distal end having at least one light-emitting segment formed therein through which light from the light source exiting the optical fiber. The optical fiber is coupled to the tube such that the at least one light-emitting segment is located substantially adjacent to the at least one opening in the wall of the tube, whereby at least a portion of the light exiting the optical fiber through the at least one opening can be detected externally for guiding placement of the tube in the lumen. The light emitting segment and the opening are disposed can be disposed in registration with each other.

According to another practice, the tube can include a plurality of openings formed in a wall thereof, where the optical fiber includes at least one light-emitting segment for emitting light received from the light source, and wherein the light-emitting segment is disposed in registration with one of the plurality of openings.

The tube can include a plurality of openings formed in a wall thereof, and the optical fiber can include a plurality of light-emitting segments for emitting light received from the light source, wherein each of the light-emitting segments is disposed in registration with one of the plurality of openings.

According to one embodiment, the illumination system can be configured such that the tube corresponds to a nasogastric device. The tube has a proximal end and a distal end and is configured for placement in an individual's gastrointestinal tract, where the tube has at least one opening in a wall thereof. The nasogastric device further includes at least one fiber optic (herein also referred to as an optical fiber) extending from a proximal end configured for receiving light from a light source to a distal end through which the light exits the fiber optic, the fiber optic having at least one light-emitting segment through which light exits the fiber optic, the fiber optic being coupled to said tube such that said at least one light-emitting segment of the fiber optic is located substantially adjacent to said at least one opening in the tube wall, whereby at least a portion of the light exiting the fiber optic through said at least one opening passes through said opening and propagates through tissue to be detected externally for guiding deployment and placement of the nasogastric feeding tube in the individual's gastrointestinal tract.

In some embodiments, the nasogastric device can be a nasogastric feeding tube, which includes a passageway for administration of nourishment and/or medicine to a patient. In other embodiments, a nasogastric device according to the present teachings can be used for other purposes. For example, the nasogastric device can include a passageway to which a negative pressure can be applied for decompressing the stomach for surgery and/or to prevent nausea/vomiting.

In some embodiments, one or more light-emitting segments of the fiber optic can be positioned in a distal region of the fiber. In some such embodiments, one or more light-emitting segments of the fiber optic can be configured so as to provide side emission of the light. In some embodiments, one or more light-emitting segment(s) of the fiber optic can be configured to emit light from the distal end of the fiber optic. In some such embodiments, the light is emitted along an axial direction of the fiber optic with the divergence of the emitted light resulting in at least a portion of the light being observed externally in such a way as to allow guiding the tube along the patient's gastrointestinal tract. Further, in some embodiments in which the light is emitted from the distal end of the fiber optic, the distal region of the fiber optic is bent so as to be in substantial register with an opening in the tube, thereby enhancing the optical coupling between the light emitted by the fiber and that opening.

In some embodiments, the tube of a nasogastric device according to the present invention can include a plurality of openings and the fiber optic can include a plurality of light-emitting segments. In some such embodiments, the fiber optic is disposed within the tube such that each of the plurality of light-emitting segments is in substantial register with one of the openings in the tube so as to emit light in a plurality of directions in order to facilitate the placement of the tube within a patient's gastrointestinal tract. In some embodiments, the plurality of openings are disposed in the tube so as to allow monitoring the tube regardless of its rotational orientation as it is being guided along a patient's gastrointestinal tract. By way of example, the plurality of openings can be distributed substantially uniformly around a cross-sectional circumference of the tube.

In some embodiments, the fiber optic can be attached, e.g., glued, to an inner surface of the tube's wall. Such placement of the fiber optic can advantageously facilitate monitoring the tube via transillumination.

The tube can be formed of a variety of different polymeric materials. In general, any suitable polymeric material can be used. Some examples of such materials include, without limitation, silicone rubber, and polyurethane.

The nasogastric device can further include a light source that is optically coupled to the optical fiber to provide light thereto. For example, the light source can be coupled to the proximal end of the optical fiber to deliver light to the fiber. A variety of light sources can be employed in the practice of the invention. Some examples of suitable light sources include, without limitation, a light-emitting diode (LED), a laser diode, and an incandescent light source, among others. While in some embodiments, the light source can emit visible radiation, in other embodiments, the light source can emit radiation in the near-infrared region of the electromagnetic spectrum. Further, while in some embodiments, the emitted light can be white light, in other embodiments, the light source can emit substantially monochromatic light, e.g., red light. In some embodiments, the light source can emit light with wavelengths in a range of about 810 nm to about 850 nm.

In some embodiments, the optical fiber is a single-mode fiber while in other embodiments, it can be a multi-mode fiber. The optical fiber can have, for example, a diameter in a range of about 0.5 mm to about 2 mm, though other diameters can also be used so long as the fiber can be inserted within the nasogastric tube.

In some embodiments, an external detector can be utilized to detect externally the light emitted by the optical fiber so as to allow guiding the fiber through the patient's gastrointestinal tract. For example, in some such embodiments, a camera can be employed to the detect the light passing through the tissue. In some such embodiments, the camera can be a visible or an infrared camera.

In a related aspect, a nasogastric device is disclosed, which includes a tube having a proximal end and a distal end and is configured for placement in an individual's gastrointestinal tract. The tube can include a tubular side wall that is configured for receiving, at its proximal end, light from a light source. The tubular side wall is substantially transparent to the received light such that the light is partially transmitted along the tubular wall and is partially transmitted to external environment via passage through an outer surface of the tubular wall to be detected externally after passage through tissue for guiding deployment and placement of the nasogastric feeding tube in the individual's gastrointestinal tract.

In some embodiments, the nasogastric device can be a nasogastric feeding tube, which includes a passageway for administration of medicine and/or nourishment to a patient. In other embodiments, a nasogastric device according to the present teachings can be used for other purposes. For example, the nasogastric device can include a passageway to which a negative pressure can be applied for decompressing the stomach for surgery and/or to prevent nausea/vomiting.

By way of example, the tubular wall can be formed of clear silicone rubber, or any other suitable material.

In some embodiments, a plurality of light sources are optically coupled to the proximal end of the tubular wall to deliver light from multiple points to the tubular wall so as to ensure that substantially the entire tubular wall is illuminated. This can allow for external monitoring of the tube regardless of its rotational orientation in the individual's gastrointestinal tract.

In a related aspect, a nasogastric feeding device is disclosed, which includes a tube having a proximal end and a distal end and configured for placement in an individual's gastrointestinal tract. A light-emitting diode (LED) is coupled to the tube such that at least a portion of the light emitted by the LED passes through the opening. At least a portion of the light passing through the opening can pass through at least a portion of the surrounding tissue to be detected externally for guiding the deployment and placement of the nasogastric tube in the individual's gastrointestinal tract. For example, the LED can be positioned in the distal region of the feeding tube in proximity (and preferably in substantial register) with the opening in the distal region of the tube to allow efficient coupling of the light emitted by the LED into the tube's opening. A plurality of conductors extending through the tube can be coupled to the LED to supply electrical power thereto. In some embodiments, the conductors can be placed within an electrically insulating sleeve.

In yet another aspect, a gastrointestinal feeding device is disclosed, which includes a feeding tube having a proximal end and a distal end. A lens is coupled to the distal end of the tube. Further, an optical fiber is positioned in the tube such that its distal end is optically coupled to the lens. A light source can be used to deliver light to a proximal end of the optical fiber. The light can be emitted by the optical fiber at its distal end to be coupled to the lens. In some embodiments, a divergent lens is employed, which can cause divergence of the light received from the optical fiber such that at least a portion of the light is transmitted through at least a portion of the surrounding tissue to be monitored externally (e.g., via visualization and/or via an external detector (such as a camera)). The lens can be formed of a variety of different materials, such as a variety of suitable polymeric materials.

In a related aspect, a nasogastric device is disclosed, which includes a tube having a proximal end and a distal end and configured for placement in an individual's gastrointestinal tract, said tube having a window in a wall thereof, and at least one fiber optic having a proximal end configured for receiving light from a light source and a distal end, where the fiber optic has at least one light-emitting segment. The fiber optic is coupled to the tube such that said at least one light-emitting segment of the fiber optic is located substantially adjacent to said at least one window in the tube wall, whereby at least a portion of the light exiting the fiber optic through said at least one opening can be detected externally for guiding deployment and placement of the nasogastric tube in the individual's gastrointestinal tract.

In some embodiments, the window is substantially transparent to the light emitted by the fiber optic. In some embodiments, the tube includes a plurality of windows through one or more of which the light emitted by the fiber optic transilluminate at least a portion of the tissue surrounding the tube. In some embodiments, the window can include a color filter. In some embodiments, the nasogastric device is configured for administering any of medicine and/or nourishment to a patient. In some embodiments, the nasogastric device is configured for applying suction to a patient's stomach.

Further understanding of various aspects of the invention can be obtained by reference to the following detailed description in conjunction with the associated drawings, which are described briefly below.

BRIEF DESCRIPTION OF THE DRAWINGS

These and other features and advantages of the present invention will be more fully understood by reference to the following detailed description in conjunction with the attached drawings in which like reference numerals refer to like elements throughout the different views. The drawings illustrate principals of the invention and, although not to scale, show relative dimensions.

DETAILED DESCRIPTION

Figure 1A:
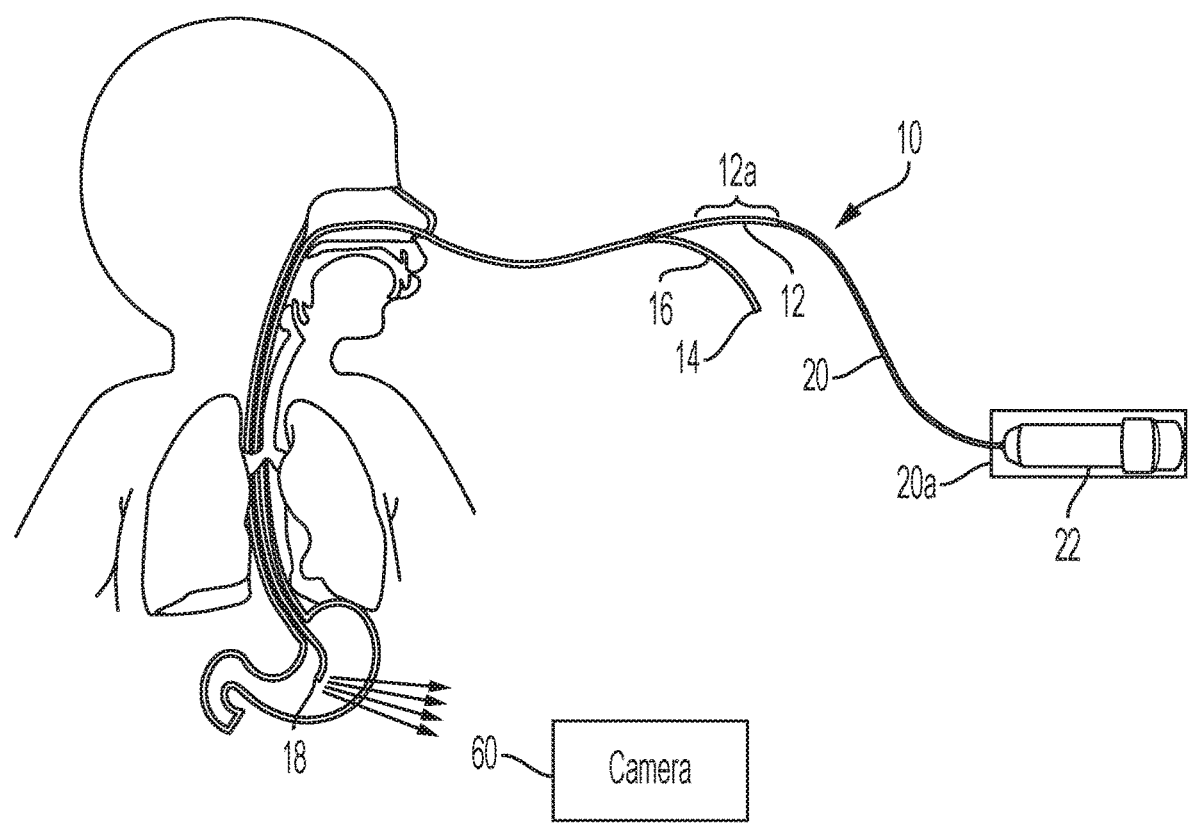
FIG. 1A schematically depicts an illumination system of the present invention that includes a tube in the form of a gastrointestinal feeding device that is coupled to an optical fiber.

The present invention generally relates to systems, methods, and devices for illuminating a lumen within a human body, and can include for example a tube for positioning in a lumen within a patient, where the tube includes at least an opening and/or a window in a distal region thereof. Such a device can include an illumination system or subsystem for delivering light to the tube such that at least a portion of the delivered light exits through the opening and/or window to be detected externally (via visualization or otherwise), thereby allowing a user to guide the placement of the tube within the lumen. As used herein, the term "lumen" is intended to include any internal passage or opening within the human body, and can include nasal passages, gastric passages and chambers, intestinal tracts and openings, esophageal passages, cardiac passages, venous, capillary and aortic passages, bronchial passages, uterine tracts and openings, and the like. According to one embodiment of the present invention, the invention allows positioning a gastrointestinal tube or a cardiac tube via transillumination. In some embodiments, the illumination subsystem can include an optical fiber that is positioned within the tube to transmit light received from a remote light source to the opening (and/or window) disposed in the distal region of the tube. In other embodiments, a light source can be positioned within the tube to deliver light to the opening (and/or window). Further, in some embodiments, a lens can be coupled to the distal end of the tube to receive light from an optical fiber positioned within the tube. In some such embodiments, the lens can be a divergent lens that causes the divergence of the light incident thereon such that at least a portion of the light would exit a portion of the surrounding tissue to be detected externally. A nasogastric device according to the present teachings can be used for a variety of different purposes. For example, in some embodiments, the nasogastric device can be configured for administering medicine and/or nourishment to a patient. In other embodiments, a nasogastric device according to the present teachings can be used for decompressing the stomach for surgery and/or to prevent nausea/vomiting. While in some embodiments discussed below, a nasogastric device according to the present teachings is configured as a nasogastric feeding device for administering nourishment and/or medicine to a patient, it should be understood that the teachings of the present invention are equally applicable to other types of nasogastric devices, e.g., those that are configured for decompressing a patient's stomach.

Various terms are used herein according to the ordinary meanings, unless indicated otherwise. The terms "light" and "radiation" are used herein interchangeably to refer not only to visible radiation but also to radiation in other regions of the electromagnetic spectrum, such as near-infrared. Further, the terms "fiber optic" and "optical fiber" are used herein interchangeably to refer to a waveguide through which electromagnetic radiation can be transmitted. The term "visible light" as used herein refers to radiation wavelengths in a range of about 400 nm to about 700 nm, the term "near-infrared radiation" refers to radiation having wavelengths in a range of about 750 nm to about 2500 nm. The term "transillumination" as used herein refers to the passage of light through a body portion, e.g., to allow guiding a tube through a body lumen.

FIGS. 1A through 1E schematically depict an illumination system that can deliver light to a specific location or site within a lumen of the human body. According to one practice, the illumination system can be configured as a nasogastric system 10 that includes a tube 12 configured for placement in a lumen of a patient, such as for example in a gastrointestinal tract for administration of enteral nutrition or compression of the stomach. The tube 12 has a proximal end 12a and a distal end 12b. In some embodiments, the tube 12 terminates in an outlet port 18. An inlet port 14 is fluidly coupled to the proximal end of the tube 12 via a tube section 16. The inlet port 14 can be configured as any suitable port, such as a sump port. In some embodiments in which the nasogastric system 10 is configured for administering nourishment and/or medicine to a patient, the outlet port 18 can be used for introducing such nourishment and/or medicine to the patient's gastrointestinal tract. In other embodiments, the outlet port 18 can be used to connect the tube to a pump, e.g., to remove air from the patient's stomach, so as to enhance visibility of any light emitted from the tube 12. The tube 12 can include a plurality of openings 30a, 30b, 30c, and 30d (herein collectively referred to as openings 30) disposed in the distal end 12b of the tube 12. As discussed in more detail below, at least one of the openings 30 can allow for the passage of light emitted from an optical fiber incorporated into an internal chamber 12d of the tube so as to allow tracking of the tube 12, such as for example by visualization or by detection via a detector, as the tube is being inserted and guided within a lumen, such as the gastrointestinal tract of the patient.

More specifically, the nasogastric system 10 includes an optical fiber 20 that can be attached to an inner wall 12c of the tube 12 and can extend from the proximal end 12a of the tube 12 to the distal end 12b. In some embodiments, the optical fiber 20 can be attached to the inner wall 12c of the tube in a variety of different ways. By way of example, as shown schematically in FIG. 1C, the optical fiber 20 can be glued to an inner wall 12c of the tube 12.

In other embodiments, the optical fiber 20 can be disposed in the tube 12 such that the optical fiber 20 can be inserted or extracted after the tube 12 is placed in the patient's gastrointestinal tract, e.g., after the distal region 12b of the tube 12 is placed within the patient's stomach and/or duodenum. For example, the optical fiber 20 can be inserted in the tube 12 without gluing or otherwise affixing the optical fiber to the tube. The illustrated optical fiber 20 has a proximal end 20a and a distal end 20b. The proximal end 20a of the optical fiber 20 is optically coupled to a light source 22. The light source 22 can have any selected size, shape or configuration, and can employ any suitable type of radiation or light element for producing the light and can be coupled to any suitable type of power source. According to one embodiment, the light source 22 can be configured as a handheld battery-operated light source that is capable of generating light. A variety of light sources emitting light in the visible and/or infrared region of the electromagnetic spectrum can be employed. In this embodiment, the handheld light source 22 includes a light emitting diode (LED). In some embodiments, white light with wavelengths in a range of 400 to 700 nm with a minimum of about 5000 CCT (Correlated Color Temperature) to about 6200 CCT can be used. Alternatively, monochromatic light (e.g., red light) or non-visible light (e.g., with wavelengths greater than 700 nm), i.e., near-infrared (700 nm-1400 nm) can be employed. In other embodiments, an LED emitting radiation in the infrared portion of the electromagnetic spectrum, e.g., in a wavelength range of about 600 nm to 2500 nm, can be employed. An example of such an LED is marketed by CREE under the trade designation Photo Red LED (XQEEPR). Further, the optical fiber can be composed of any suitable material, such as plastic.

Figure 2A:
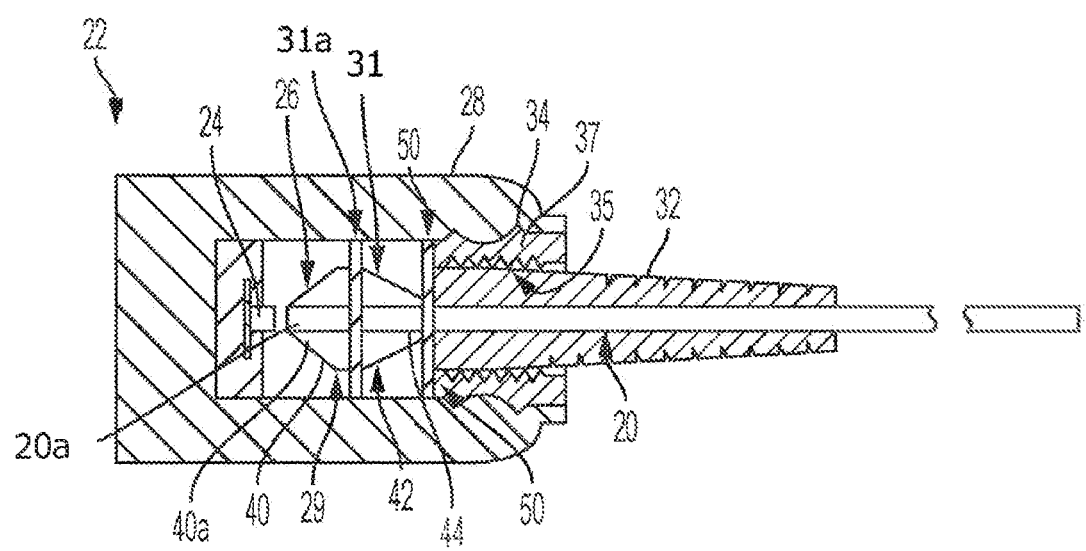
FIG. 2A schematically depicts a portion of a handheld light source depicted in FIG. 1A, indicating the positioning of an LED in an enclosure provided in the light source's housing.
Figure 2B:
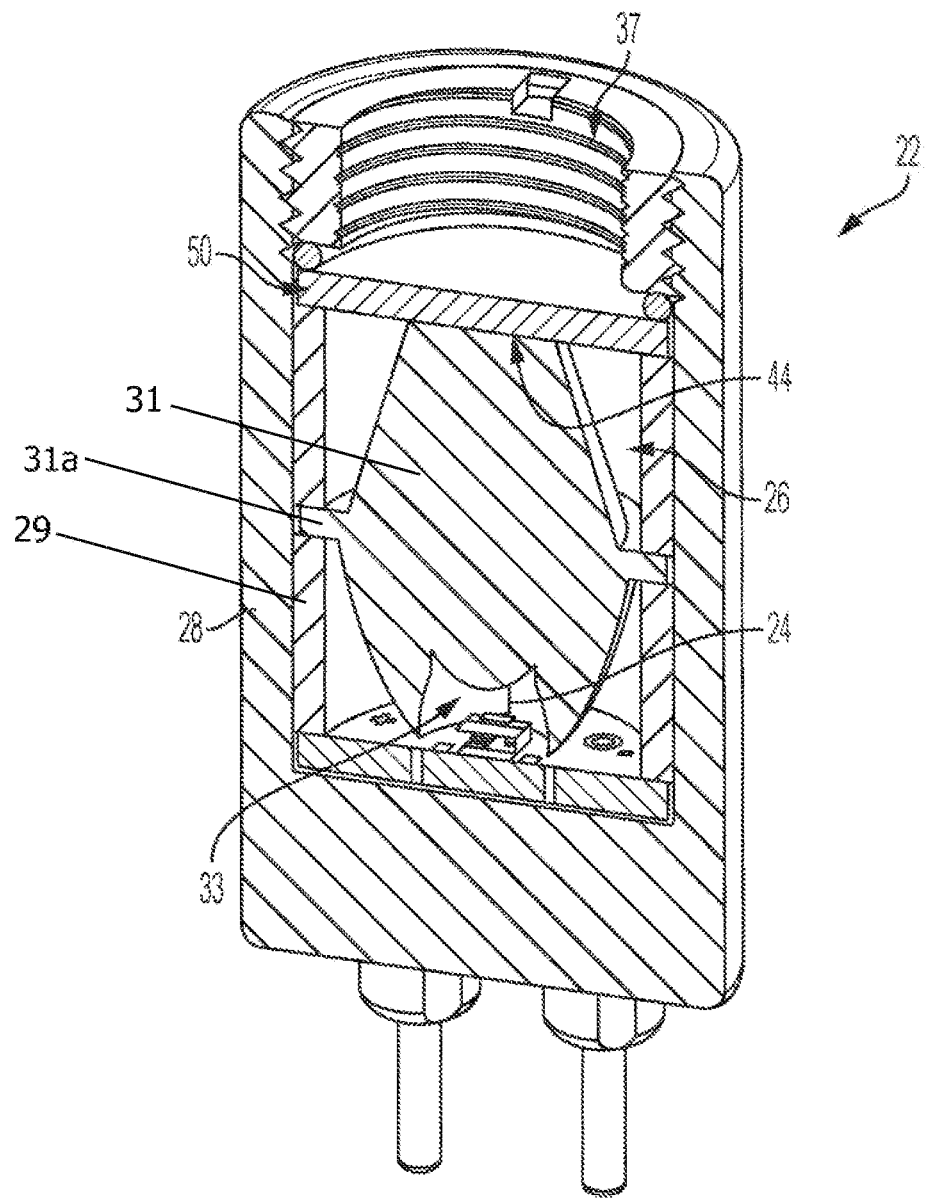
FIG. 2B schematically depicts another view of the portion of the handheld light source depicted in FIG. 1A.

With reference to FIGS. 2A and 2B, the light source 22 includes a light element, such as the LED 24 that is disposed in an enclosure 26 provided in a housing 28 of the light source. A lens 31 is also provided in the enclosure 26 and is optically coupled to the LED 24 to receive light therefrom. The housing also mounts the lens 31, which includes a collar 31a that can be seated on a shoulder 29 provided within the enclosure 26 to maintain the lens 31 in the enclosure and in optical coupling or communication with the LED 24. A fiber optic adapter 32 can be removably and replaceably received in the upper hollow cylindrical portion 34 of the housing 28 to allow coupling the optical fiber 20 to the LED 24. In this embodiment, the fiber optic adapter 32 can include a plurality of threads 35 that can engage with a plurality of mating threads 37 provided on the inner wall of the upper hollow cylindrical portion 34.

The lens 31 includes a proximal portion 40 and a distal portion 42. The proximal portion 40 of the lens includes a recess 33 through which light from the LED 24 can enter the lens. The proximal portion 40 includes a lateral surface 40a that is configured to reflect light incident thereon via total internal reflection toward the distal portion. Some of the light entering the lens via the recess 33 passes through the proximal portion of the lens without undergoing reflections at the lateral surface 40a thereof to reach the distal portion of the lens. The light passes through the distal portion of the lens and exits an output surface 44 of the lens. In this embodiment, an optical window 50 is disposed over the output surface 44 of the lens. The optical window 50 can protect the output surface of the lens and, in some embodiments, the optical window 50 can adjust one or more characteristics of the light exiting the lens. By way of example, the optical window 50 can be selected to function as a filter, e.g., a bandpass filter, to allow passage of certain wavelengths of light exiting the lens while blocking other wavelengths.

In some embodiments, the lens 31 can be configured to focus the light received from the LED 24 onto an external focal point in proximity of the input surface of the optical fiber 20 such that the divergence angle of the light propagating from the focal point to the input of the optical fiber substantially matches the numerical aperture of the optical fiber so as to allow efficient coupling of the light into the optical fiber.

Figure 3:
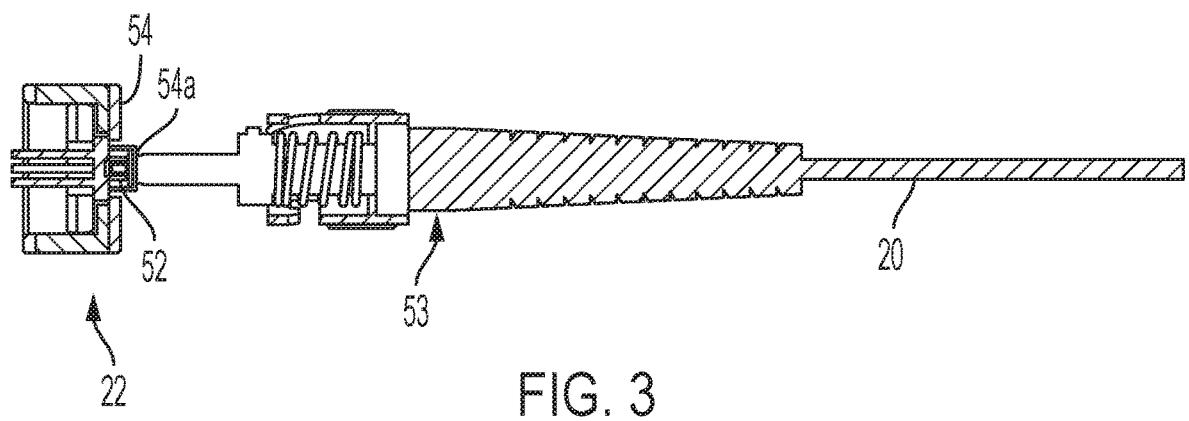
FIG. 3 schematically depicts one example of coupling an optical fiber used in a gastrointestinal feeding device to a laser diode to receive light therefrom according to the teachings of the present invention.

In other embodiments, the optical fiber 20 can be optically coupled to the light source 22 using other mechanisms. For example, with reference to FIG. 3, the light source 22 can be a laser diode 52 having a housing 54 in which an opening 54a is formed for receiving, e.g., via a friction fit, a fiber optic coupling 53 to which the optical fiber 20 can be coupled so as to receive light from the laser diode. In some cases, a flange (not shown) can be used to ensure that the proximal end of the fiber coupling 53 is securely coupled to the opening in the housing of the light source.

Figure 1B:
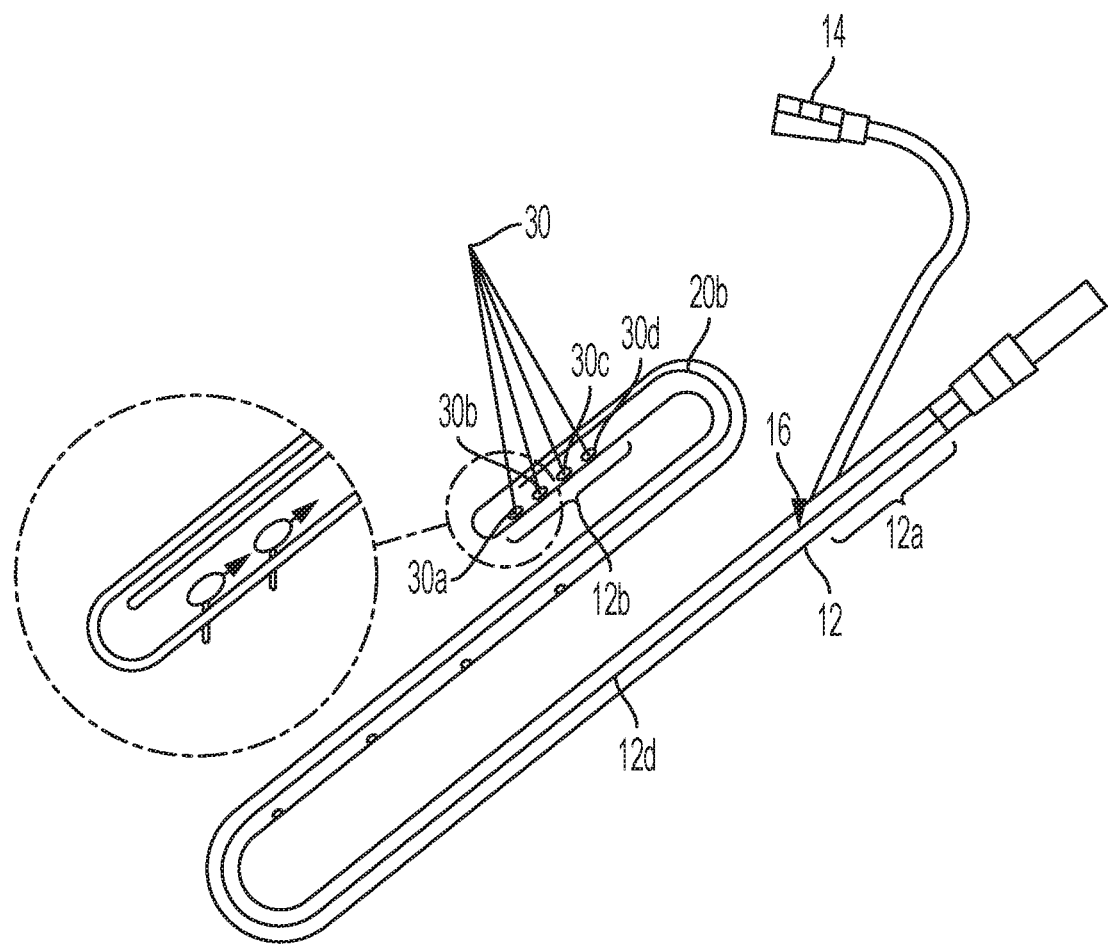
FIG. 1B schematically depicts a light-emitting segment of the optical fiber that is positioned in proximity of at least one of the plurality of openings provided in the tube through which the light emitted by the optical fiber can pass to be externally detected.
Figure 1C:
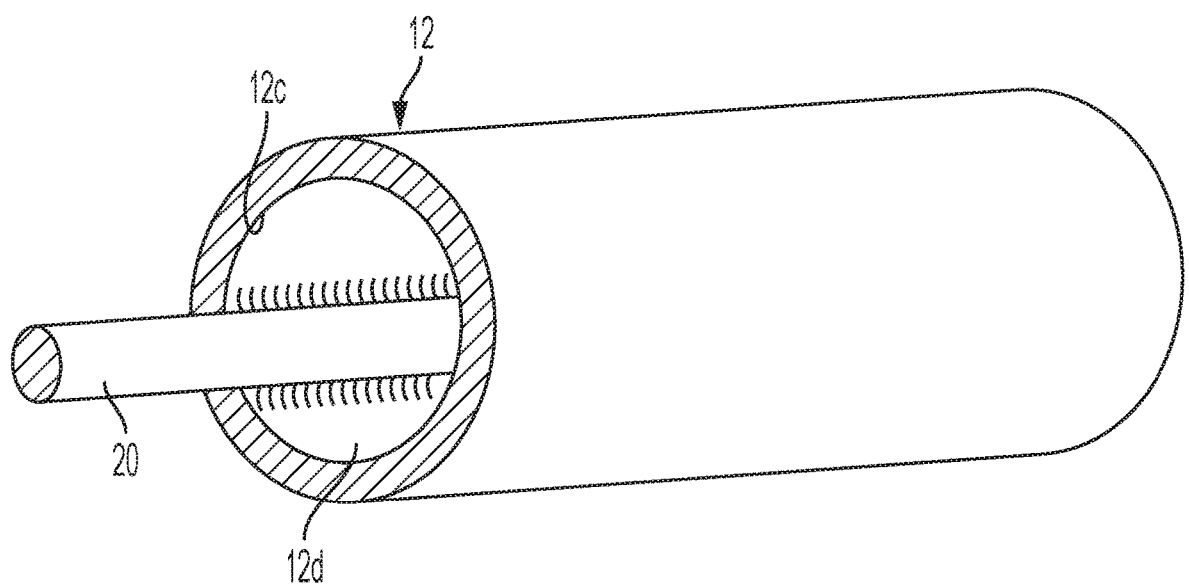
FIG. 1C schematically depicts that the optical fiber can be glued to the inner wall of the tube, FIG. 1D schematically depicts three different types of optical fibers suitable for use in various embodiments of the present invention.
Figure 4:
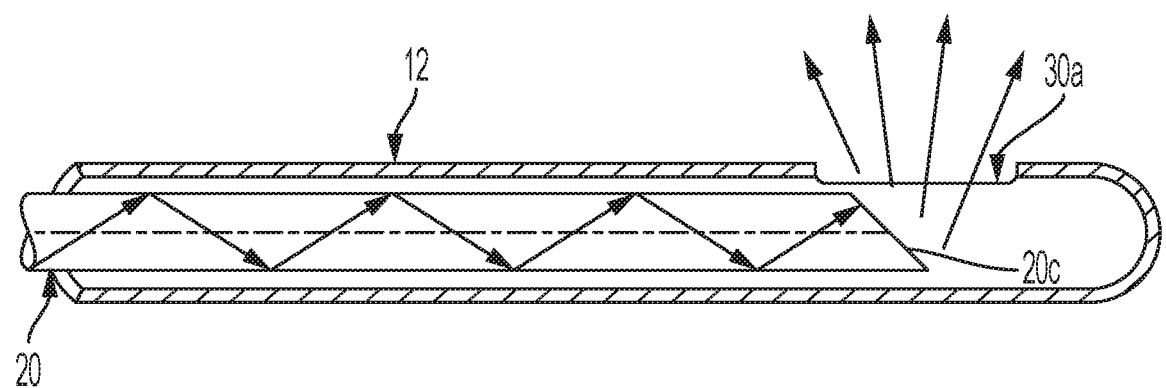
FIG. 4 schematically depicts an optical coupling of a light-emitting segment of an optical fiber to an opening provided in a tube of a gastrointestinal feeding device according to the teachings of the present invention.

With reference to FIGS. 1A, 1B, and 4, the optical fiber 20 is disposed in the tube 12 such that a light-emitting segment 20c of the fiber is in substantial register with one or more of the openings 30 (e.g., opening 30a) in the distal portion 12b of the tube 12. In other embodiments, the tube 12 can include a single opening 30 that is configured to receive light from the optical fiber. In this embodiment, the optical fiber 20 is a side-emitting fiber in which its light-emitting segment is angled at about 45 degrees relative to the axis of the optical fiber so as to direct the emitted light toward the opening 30a in the tube. At least a portion of the light emitted through the opening 30a passes through a portion of the surrounding tissue and can be monitored (e.g., visually and/or via an appropriate detector) to guide the nasogastric tube through the gastrointestinal tract.

The light emitted via the optical fiber 20 that passes through surrounding tissue can be externally detected and monitored, visually or via an appropriate detector. For example, as shown schematically in FIG. 1, a camera 60 can be employed to obtain an image of the distal portion 12b of the tube 12 to discern the position of the tube within the gastrointestinal tract.

Figure 1D:
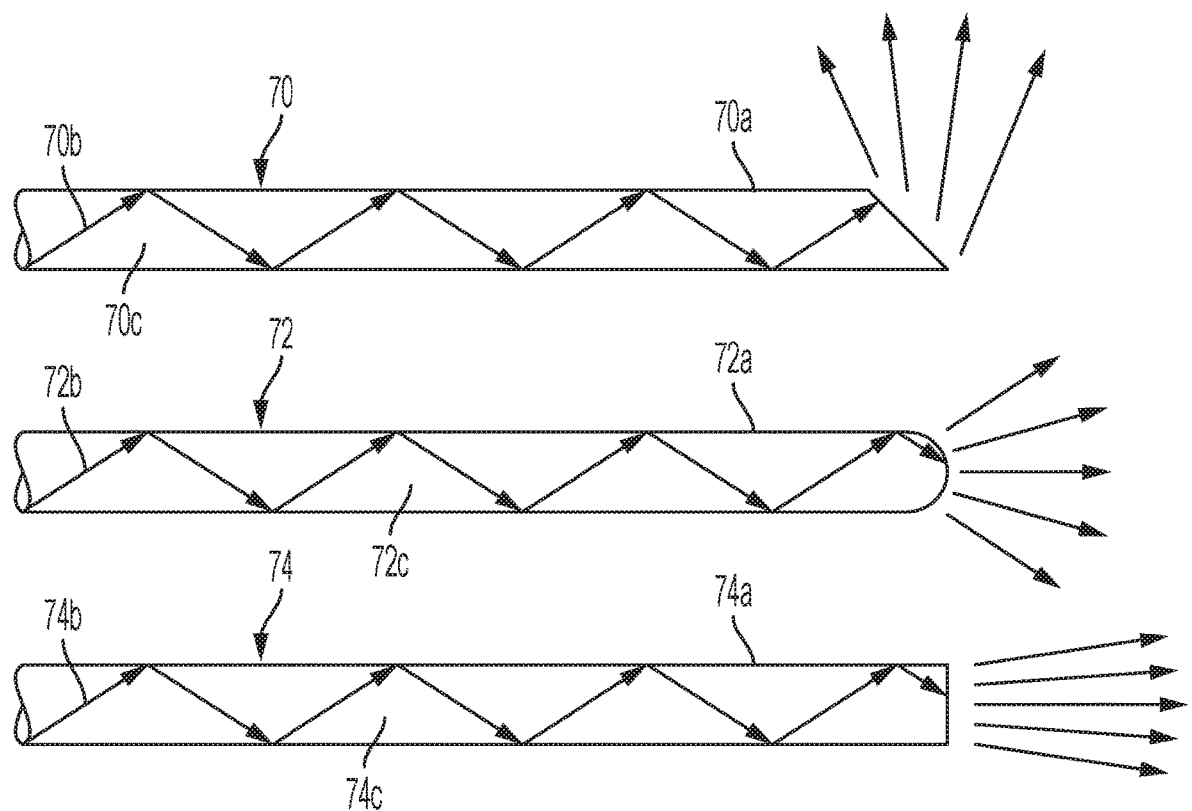
FIG. 1E schematically depicts that in some embodiments the optical fiber can be disposable.
Figure 1E:
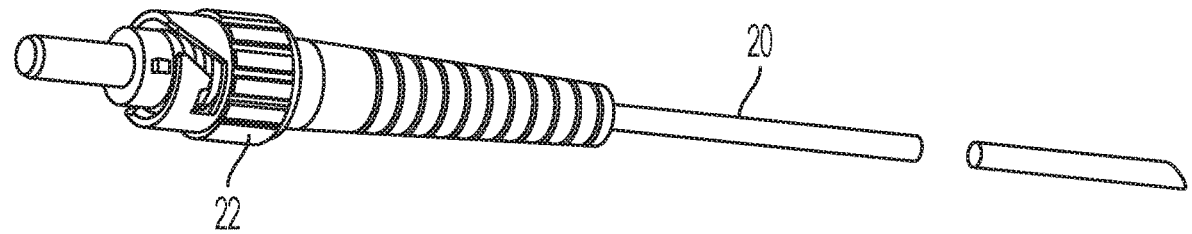

A variety of different fibers emitting light in a variety of different ways can be used in the practice of the invention. For example, FIG. 1D shows three different types of optical fibers 70, 72, and 74 suitable for use in various embodiments of the present invention. The optical fiber 70 has a distal end 70a and light rays 70b passing through an inner chamber 70c are emitted an end region formed at the distal end 70a. Specifically, the light is emitted at a 45-degree angle relative to a longitudinal axis of the fiber since the opening is slanted or formed at an angle. Likewise, the optical fiber 72 has a rounded distal light-emitting end 72a, and the light rays 72b passing through an inner chamber 72c are emitted at the distal end region 72a in a more dispersed pattern. Also, the optical fiber 74 has a substantially flat distal light-emitting end 74a and light rays 74b passing through an inner chamber 74c are emitted at the distal end 70a in a relatively parallel manner. Other optical fiber configurations can also be used, such as for example fibers that have multiple light-emitting segments that are distributed along their length, where each of the light-emitting segments can be positioned in substantial registration with one of a plurality of openings disposed in the distal region of the tube, as discussed in more detail below. With reference to FIG. 1E, in some embodiments, the optical fiber 20 can be disposable and hence can be removed, after use, from the light source 22. The tube can be discarded as well.

Referring again to FIG. 1A, the illumination system can be configured as a nasogastric system that employs the tube 12 and the associated optical fiber 20. The distal end 12b of the tube 12 can be positioned in the esophagus of the patient and can be guided to reach the patient's stomach. The optical fiber 20 is coupled to the light source 22 and hence light is conveyed from the light source 22 through the fiber to the distal end of the optical fiber and hence tube. A portion of the light emitted via the optical fiber can transilluminate at least a portion of the tissue surrounding the nasogastric tube 12, thus revealing the position of the nasogastric tube, thereby allowing a user to monitor (visually or via a detector) the tube and hence to be able to safely guide the tube 12 to the patient's stomach.

In other embodiments, the optical fiber 20 can be configured to emit radiation axially at the distal end 20b, or the optical fiber 20 can include multiple light-emitting segments 20c each of which is placed in substantial registration with one of a plurality of openings 30 in the tube 12 so as to emit light along a plurality of different directions for external detection.

As noted above, in some embodiments, subsequent to the placement of the nasogastric tube 12 within a patient's gastrointestinal tract, the optical fiber 20 used for guiding the tube 12 into position can be safely and easily removed and the tube 12 can be used for its intended purpose, e.g., to administer nourishment and/or medicine to the patient or the compress the stomach, or any other purpose.

Figure 5A:
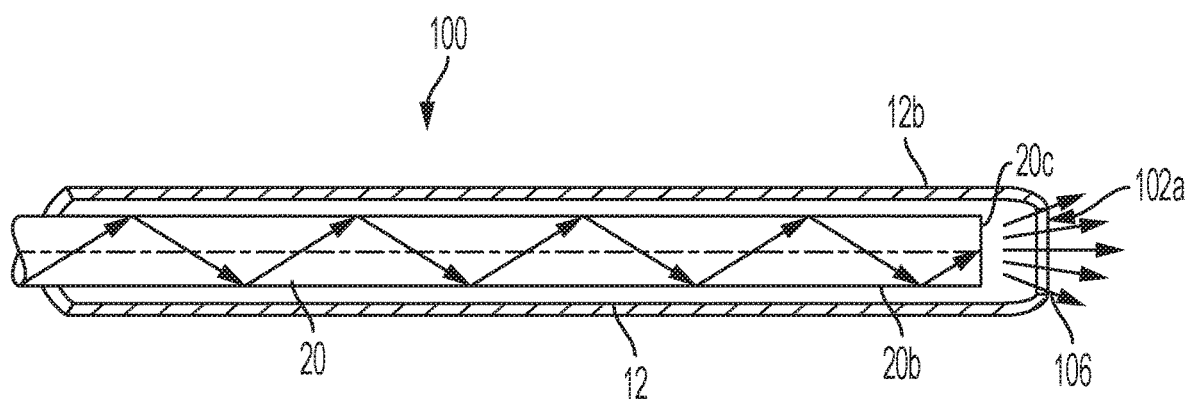
FIG. 5A schematically depicts a tube of a gastrointestinal feeding device according to an embodiment of the present invention in which the feeding tube has an opening at a distal end thereof and the optical fiber includes a light-emitting segment that is optically coupled to the distal opening of the feeding tube.
Figure 5B:
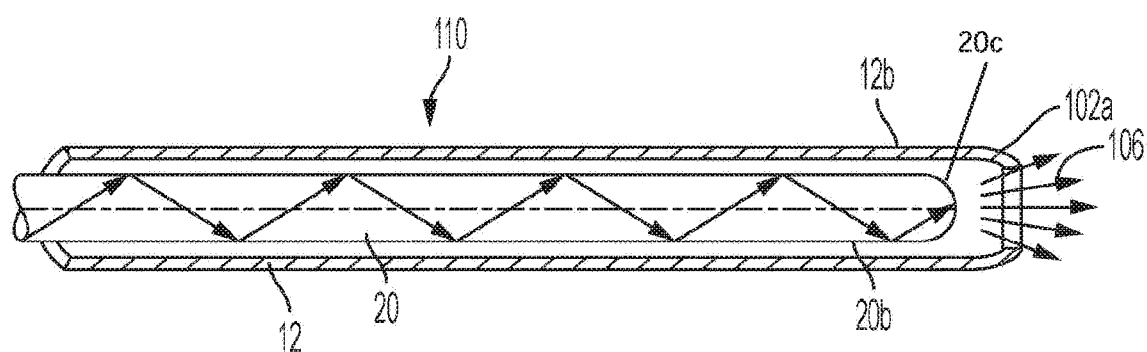
FIG. 5B schematically depicts a tube of a gastrointestinal feeding device having an optical fiber with a rounded light-emitting distal end that is optically coupled to a distal opening disposed in the feeding tube.

By way of example, FIG. 5A schematically depicts a partial view of an embodiment of a nasogastric system 100 according to the teachings of the present invention where the tube 12 includes an opening 102a at a distal end 12b, and an optical fiber 20 is disposed in the tube 12 so as to emit light 106 through the opening 102a. The optical fiber 20 includes a substantially flat light-emitting segment 20c at the distal end 20b, through which light is emitted from the optical fiber 20 and which is substantially aligned with the opening 102a to allow the passage of the emitted light 106 through the opening 102*a* for external detection. The divergence of the light 106 exiting the opening 102*a* ensures that at least a portion of the light exiting the opening 102*a* can transilluminate at least a portion of the surrounding tissue in a manner that allows monitoring the tube 12 as it is being deployed and guided within the patient's gastrointestinal tract. FIG. 5B schematically depicts another embodiment 110 in which the tube 12 seats or mounts an optical fiber 20 having a distal end 20*b* that has a rounded light emitting segment 20*c* that is disposed within the tube 12 such that the distal end 20*b* of the optical fiber is substantially aligned with the opening 102*a* to allow light 106 that is emitted from the opening 102*a* to transillumination the surrounding or adjacent tissue, thereby allowing tracking the gastrointestinal tube 12 within the patient's gastrointestinal tract.

Figure 6:
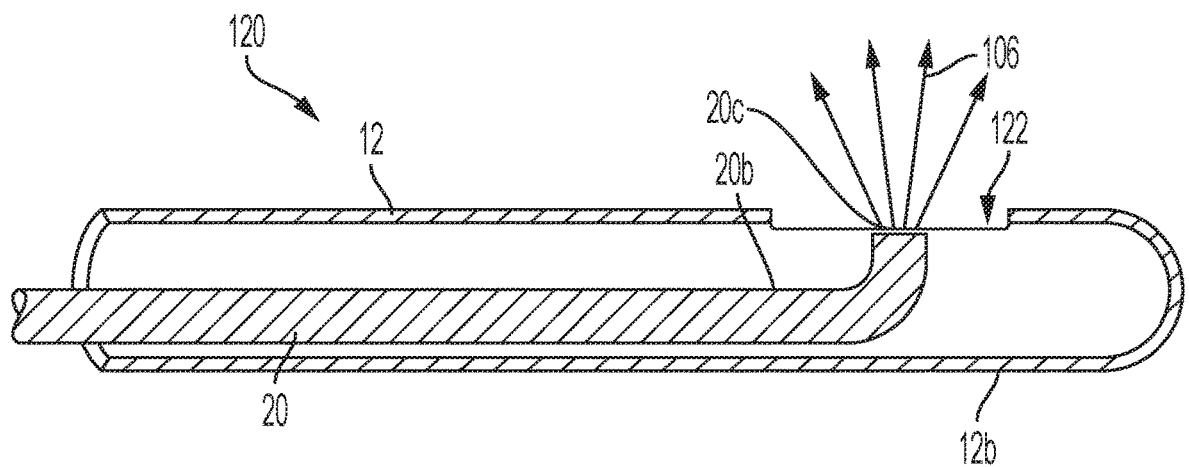
FIG. 6 schematically depicts a tube of a gastrointestinal feeding device according to an embodiment having an optical fiber with a bent light-emitting distal end that is optically coupled to an opening disposed in a side wall of the tube.

FIG. 6 schematically depicts another embodiment of a nasogastric system 120 according to the teachings of the present invention. The system includes a tube 12 (e.g., a feeding tube) in which an optical fiber 20 is disposed. In the illustrated system 120, the tube 12 includes a side opening 30, 122 at a distal end 12*b* thereof and the optical fiber 20 includes a light-emitting segment 20*c* at a distal end 20*b* through which light 106 is emitted from the optical fiber. In this embodiment, the distal end 20*b* of the optical fiber 20 is angled or bent so as to dispose the distal light-emitting segment 20*c* in substantial registration with the opening 30, 122 in the tube.

Figure 7A:
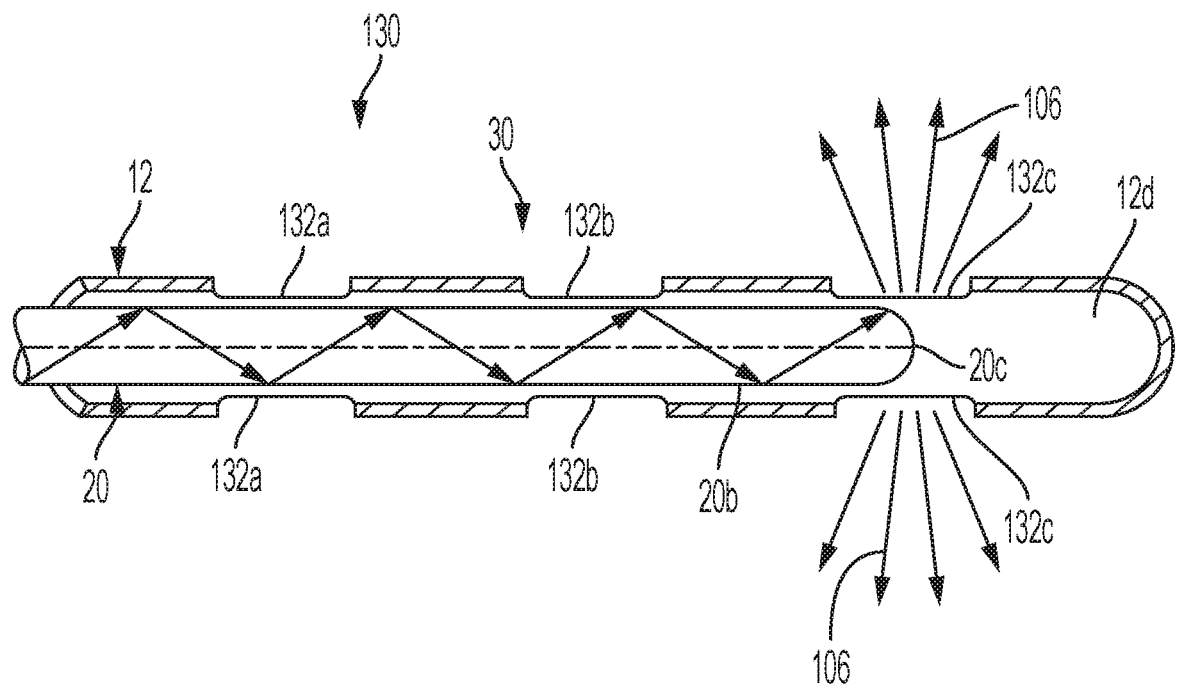
FIG. 7A schematically depicts a tube according to an embodiment of the present teachings in which a fiber optic is disposed such that the light emitted from the distal end of the fiber optic passes through two of a plurality of openings provided in the tube for transillumination of at least some of the tissue surrounding the tube for facilitating the placement and guidance of the tube within a lumen of the patient.

By way of further illustration, FIG. 7A depicts yet another embodiment of a nasogastric system 130 that includes a tube 12, which functions as a nasogastric feeding apparatus, having multiple openings 30 formed therein. The openings 30 include openings 132*a*, 132*b*, and 132*c*. The system also includes an optical fiber 20 that is mounted within the internal chamber 12*d* of the tube 12 and has s single light emitting segment 20*c*. The optical fiber 20 that is disposed in the tube 12 emits light 106 at a distal end 20*b* such that the emitted light 106 exits the tube 12 through the openings 132*c* so as to transilluminate at least a portion of the surrounding tissue and allows the nasogastric system and specifically the tube 12 to be externally monitored either visually or via a light-detecting device. In this embodiment, the other openings 132*a*, 132*b* can be used, for example, for administering nourishment and/or medicine to the patient, or to apply suction to the stomach.

Figure 7B:
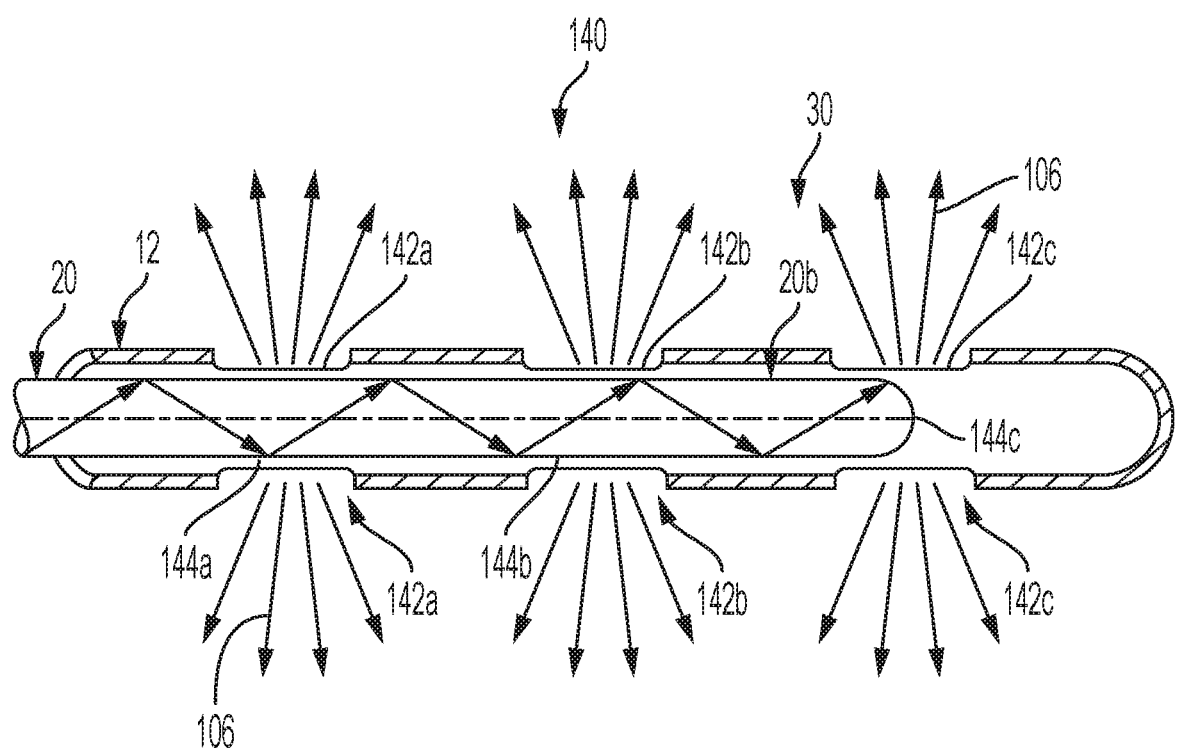
FIG. 7B schematically depicts a tube having a plurality of openings and an optical fiber disposed in the tube and having a plurality of light-emitting segments, each of which is in optical coupling with one of the openings disposed in the tube.

FIG. 7B depicts still another nasogastric system 140 having a tube 12, such as a feeding tube, having a plurality of openings 30 formed therein. The openings include openings 142*a*, 142*b*, and 142*c*. In this embodiment, the optical fiber 20 includes a plurality of light-emitting segments 144*a*, 144*b*, and 144*c*, each of which is in substantial register with one of the openings 142*a*, 142*b*, 142*c*. Similar to the previous embodiment, the light-emitting segment 144*c* is disposed at the distal end 20*b* of the optical fiber. The light-emitting segments 144*a* and 144*b* are disposed along the length of the optical fiber by removing a portion of the fiber's cladding. In this embodiment, the light-emitting segments 144*a*, 144*b* are in the form of circular bands of illumination, although in other embodiments other patterns of illumination can also be employ. The light emitting segments emit the light rays 106 that pass through the openings 30.

Figure 7C:
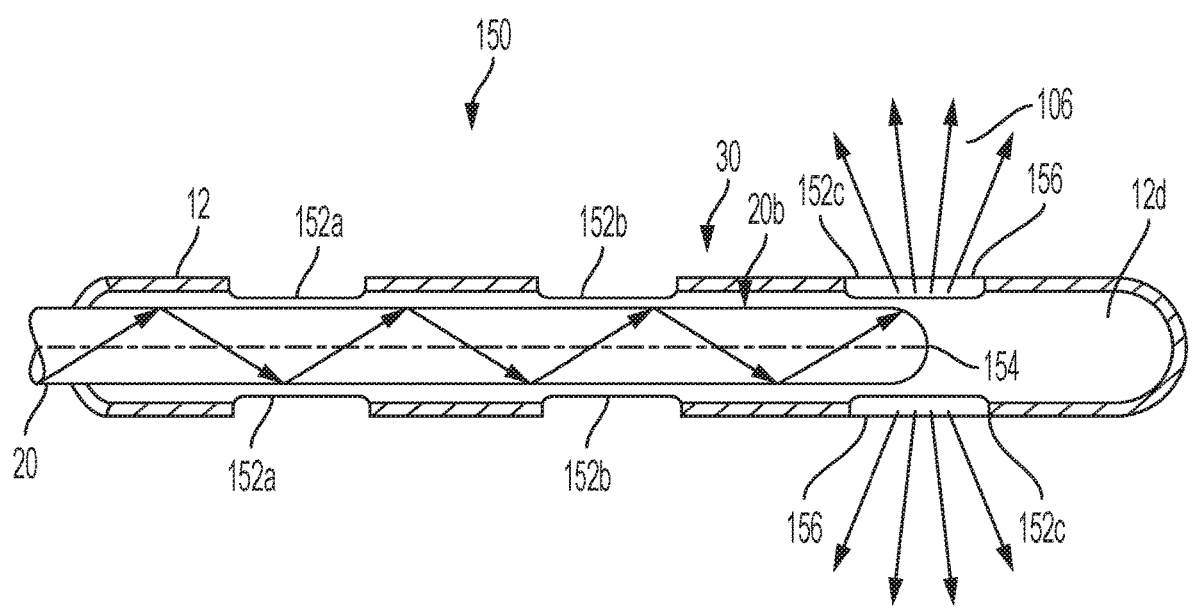
FIG. 7C schematically depicts an embodiment of the illumination system of the present invention having two windows through which the light emitted by an optical fiber disposed in the tube can exit the tube to transilluminate at least a portion of the surrounding tissue and further having a plurality of openings.

FIG. 7C schematically depicts yet still another embodiment of a nasogastric system 150 according to the teachings of the present invention. The illustrated system 150 includes a tube 12 that includes a plurality of openings 30 formed therein. The openings include openings 152*a*, 152*b*, and 152*c*. The tube 12 seats or mounts an optical fiber 20 in the tube chamber 12*d*. The optical fiber has a distal end 20*b* that includes a light emitting segment 154. The optical fiber 20 is positioned within the tube 12 such that the light-emitting segment 154 is disposed in proximity of the openings 152*c* that are formed in the distal portion 12*b* of the tube 12. The openings 152*c* have mounted therein a window element 156 that can be formed of a material that is substantially transparent to the wavelength(s) of radiation emitted by the optical fiber. By way of example, the window element 156 can be formed of transparent silicone rubber. Further, in some embodiments, at least one of the window elements 156 can function as a color filter to preferentially allow certain radiation wavelengths to pass therethrough. For example, the window can be formed from transparent silicone rubber impregnated with appropriate dye(s) to function as a color filter. The openings 152*a* and 152*b* formed in the distal region of the tube can be employed to administer medicine and/or nourishment to a patient. In other embodiments, the openings can be employed to apply suction to the patient's stomach, e.g., to compress the stomach.

Figure 7D:
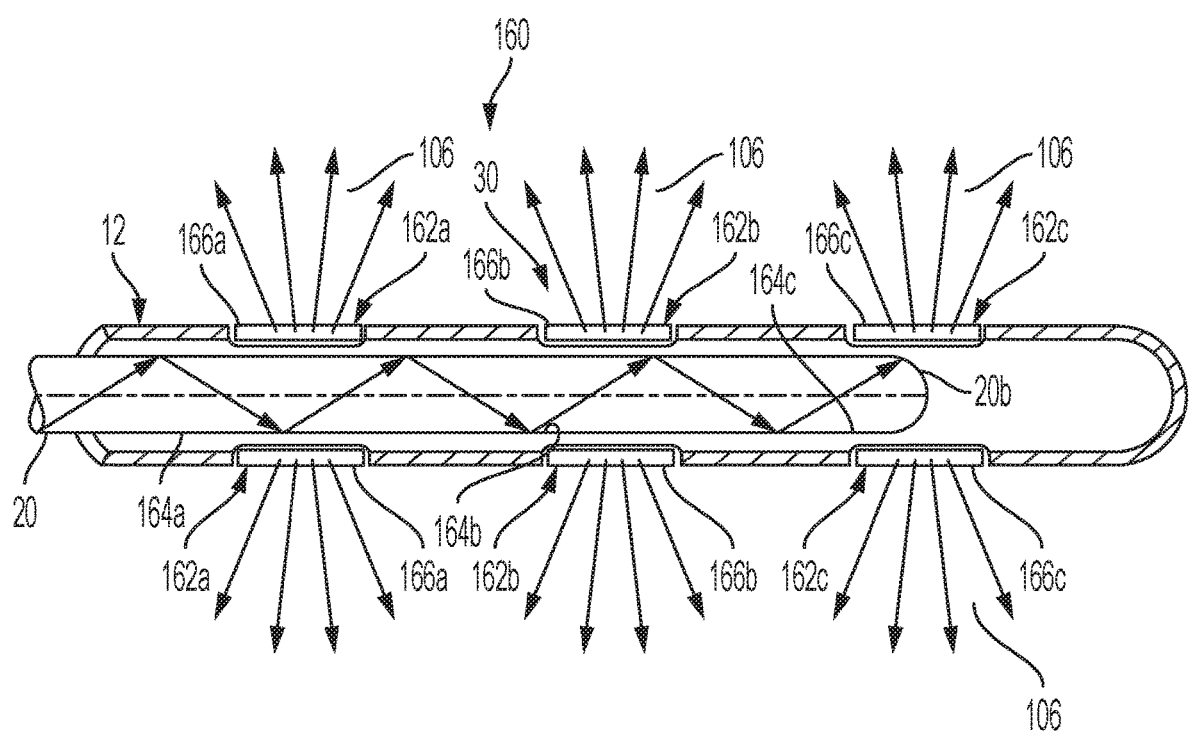
FIG. 7D schematically depicts an embodiment of the illumination system of the present invention where the tube has openings mounting a window element through which the light emitted by a fiber optic disposed in the tube can exit the tube to transilluminate at least a portion of the surrounding tissue.

FIG. 7D schematically depicts still another embodiment of a nasogastric system 160, which includes a tube 12 and an optical fiber 20 disposed in the tube 12. The tube 12 has a plurality of openings 30 formed therein. The openings include openings 162*a*, 162*b*, and 162*c*. In this embodiment, the tube 12 also includes a plurality of window elements 166*a*, 166*b*, 166*c*. The optical fiber 20 has formed at a distal end 20*b* a plurality of light-emitting segments 3002*a*, 3002*b*, and 3002*c*, where the light-emitting segment 164*a* illuminates the window element 166*a*, the light-emitting segment 164*b* illuminates the window element 166*b*, and the light-emitting segment 164*c* illuminates the window element 166*c*. The light 106 passing through the windows can transilluminate at least a portion of the lumen and surrounding tissue of the patient so as to be monitored externally (e.g., via visualization and/or detection). In some embodiments, the window elements 166*a*, 166*b*, 166*c* can function as color filters. Further, in some such embodiments, different windows can be configured as color filters for preferentially transmitting different colors of light. By way of example, in some embodiments, the windows 166*a* can preferentially transmit blue light, the windows 166*b* can preferentially transmit green light, and the windows 166*c* can preferentially transmit red light. By way of example, such an embodiment can be used with a light source emitting white light such that different segments of the nasogastric tube corresponding to the different windows can be visualized (or detected) in a different color.

Figure 8:
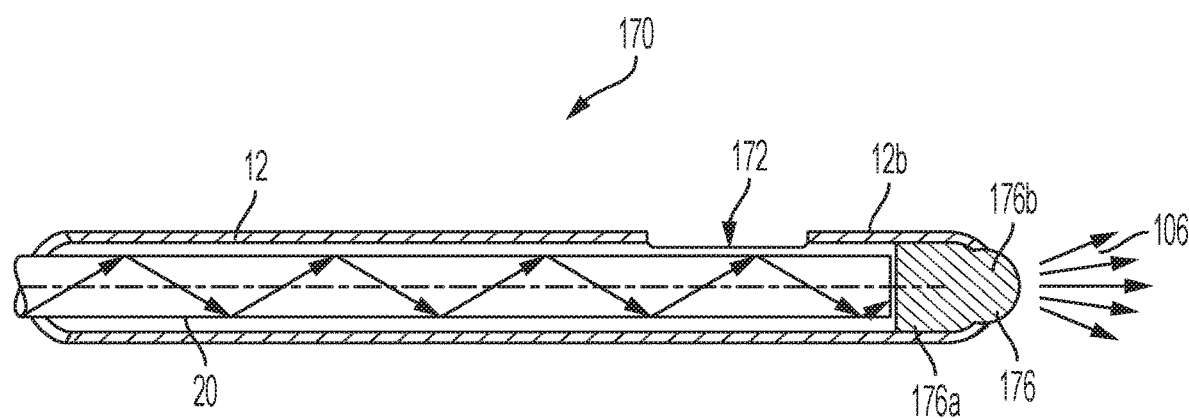
FIG. 8 schematically depicts an embodiment of the illumination system of the present invention where the tube includes a lens disposed at a distal end thereof for receiving light from an optical fiber positioned in the tube.

FIG. 8 is a partial schematic view of a nasogastric system 170, for example, a nasogastric feeding device, according to another embodiment of the present invention. The system 170 can include a nasogastric tube 12 in which an optical fiber 20 is disposed. A lens 176 is attached to a distal end 12*b* of the tube 12 and is in optical communication with a distal end 20*b* of the optical fiber 20 so as to receive light therefrom. The lens 176 includes a substantially cylindrical shaft 176*a* that extends to a hemispherical tip 176*b*. The hemispherical tip 176*b* presents a concave surface to the incident light and hence causes divergence of the incident light 106 such that at least a portion thereof exits the tissue surrounding the feeding tube to be monitored externally (e.g., via visualization or by a detector) for guiding the nasogastric tube through the gastrointestinal tract. In some embodiments, the lens 176 can be formed of a suitable polymer, such as, optical silicone rubber, PMMA (poly methyl methacrylate), polycarbonate, or glass. The nasogastric tube 12 further includes an opening 172. In some embodiments, the opening 172 can be used to administer medicine and/or nourishment to the patient. In other embodiments, the opening 172 can allow the application of suction to a patient's stomach.

Figure 9:
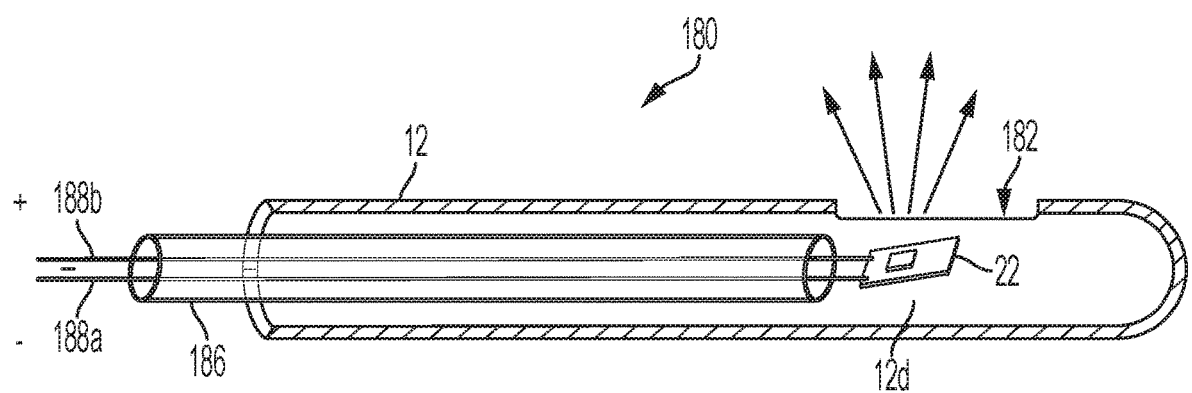
FIG. 9 schematically depicts an embodiment of the illumination system of the present invention where a light source (e.g., an LED) disposed in proximity of an opening provided in the tube to transilluminate a patient's tissue to allow safe positioning of the device in the patient's gastrointestinal tract.

FIG. 9 is a partial schematic view of another embodiment of a nasogastric system 180, e.g., a nasogastric feeding device, that includes a tube 12, e.g., a feeding tube. The tube 12 includes an opening 182 disposed in a distal region thereof. In this embodiment, rather than using an optical fiber to transmit light from a light source to the distal region of the tube, a light source 22, e.g., an LED, is disposed in the inner chamber 12d of the tube 12 in proximity to the opening 182 such that at least a portion of the light emitted by the light source passes through the opening to be monitored externally (e.g., via visualization or via a detector) for guiding the tube through the lumen, such as for example the gastrointestinal tract. As shown schematically in FIG. 9, a pair of conductors the 188a/188b can extend through the tube 12 to the light source 22 to transmit electrical power from an external source, such as an external voltage source (not shown) to the light source 22. In this embodiment, the conductors 188a/188b are positioned within an electrically insulating sleeve 186. Further, in this embodiment, the light source 22 is titled toward the opening 182 so as to optimize optical coupling between the light source and the opening. In this embodiment, the opening 182 can also be employed, for example, to administer medicine and/or nourishment to the patient, or apply suction to the patient's stomach, or for other purposes. Further, in some implementation of the nasogastric system 180, rather than a single opening, multiple openings/windows can be employed, e.g., in a manner discussed above in connection with the previous embodiments.

Figure 10:
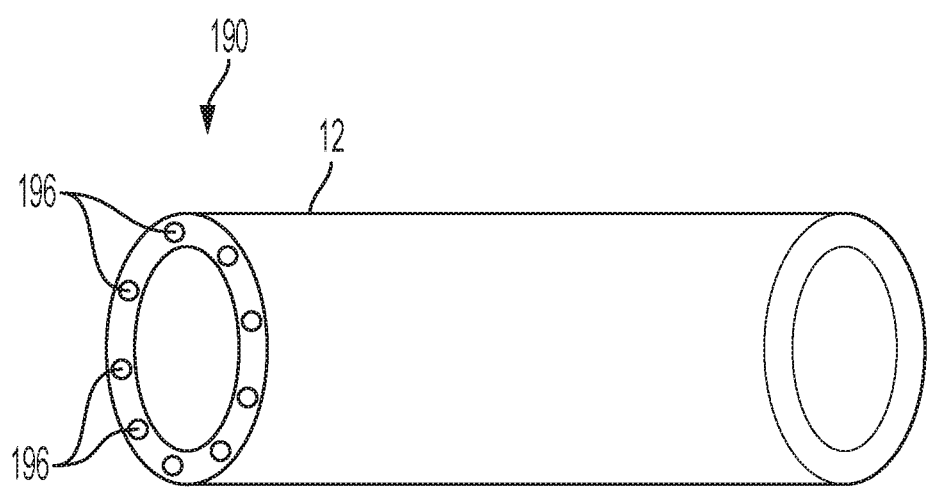
FIG. 10 schematically depicts an embodiment of the illumination system of the present invention where the tube is configured for receiving at a proximal end thereof light from one or more light sources.

FIG. 10 schematically depicts another embodiment of a nasogastric system 190 according to the present invention. The system 190 includes a tube 12, e.g., a feeding tube, having an annular shape and a plurality of light sources 196 (e.g., a plurality of LEDs) formed in the housing of the tube (as shown), and are positioned circumferentially about the tube housing. The light sources can be optically coupled to the annulus portion of the feeding tube at a proximal end thereof. Similar to the previous embodiments, the light sources 196 can generate radiation in the visible, near-infrared or infrared portions of the electromagnetic spectrum. In this embodiment, the nasogastric tube 12 is formed of a material that is substantially transparent to the radiation emitted by the light sources 196. By way of example, in some embodiments, the tube is formed of clear silicone rubber. While in some embodiments, the nasogastric device 190 can be configured as a nasogastric feeding device, in other embodiments, the nasogastric device 190 can be configured for other purposes, e.g., to compress the patient's stomach.

At least a portion of the light emitted by the light sources 196 is transmitted along the annulus of the tube and at least a portion of the light exits the annulus at it propagates from the proximal end of the tube to its distal end. Further, a portion of the light exits the annulus at the distal end thereof. At least a portion of the light exiting the annulus can penetrate through the surrounding tissue to be monitored externally (e.g., via visualization or otherwise), e.g., in a manner discussed above.

As noted above, a variety of light sources can be employed in nasogastric devices according to the teachings of the present invention. By way of example, in some cases, the light source can be a strobe light source (e.g., a strobe LED) that can provide repetitive flashes of radiation. Such flashes of radiation can be effective in capturing the attention of an operator of the device.

A nasogastric device according to the present teachings provides a number of advantages. In particular, it allows safe placement of a nasogastric tube in a patient's gastrointestinal tract without the need to expose the patient to potentially harmful radiation. This can be particularly advantageous for pediatric patients. Further, a nasogastric feeding device according to the present teachings is easy to use.

Figure 11:
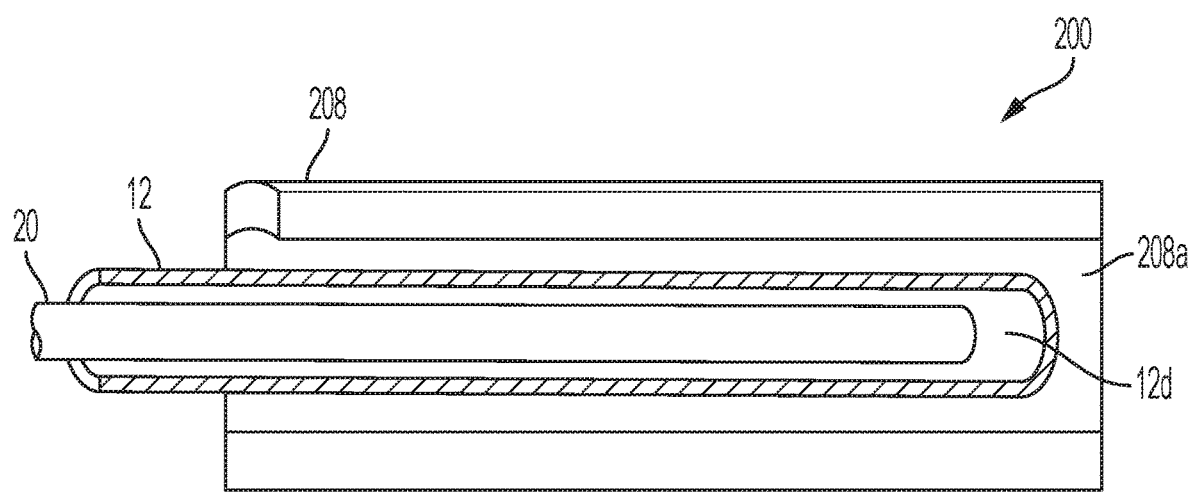
FIG. 11 is a schematic depiction of the illumination system of the present invention where the tube is configured as a catheter for mounting within a lumen, such as a vein, of the patient during a cardiac procedure.

The illumination system of the present invention can be used to illuminate or transilluminate other types of lumens and areas within the patient. For example, the above embodiments are directed to illuminating nasal and gastric passages or lumens within the body. Likewise, the illumination system of the present invention can be used to illuminate lumens in other regions of the body, including cardiac passages or lumens, including for example, venous, aortic, and capillary lumens or passages. For example, the illumination system of the present invention can also be used to locate or visually show the location of a device inserted within a lumen in the heart region of the patient. FIG. 11 illustrates a lumen 200, such as an artery or a vein 208 that exists within the body of the patient. The vein 208 has an interior chamber 208a that seats a venous tube 12 suitable for use with the present invention. The tube 12 can be a catheter or the like that is sized and configured to be inserted and then eventually positioned within a cardiac region of the patient. The tube 12 can be inserted and positioned within the patient according to known techniques. As shown in the previous embodiments, the illumination system of the present invention includes an optical fiber 20 that is coupled to a light source 22. The light source 22 can be remotely positioned external of the patient or can be disposed within the patient. The optical fiber 20 can be positioned within the chamber 12d of the tube 12 as it is inserted within one or more lumens 208 of the body. The optical fiber 20 emits light that is received from the attached light source 22 so as to illuminate the area at the distal end of the tube 12, which can be formed of a substantially transparent material through which the light can exit the tube 12 and be observed externally to allow a doctor to determine the precise position of the tube as it navigates or passes through the body. The illumination system allows the doctor to visually determine the precise location of the tube, thus enabling the doctor to precisely locate and position the tube at a selected site within the lumen. In other embodiments, other portions of the tube 12 can be substantially transparent (such as the sections discussed above in connection with the previous embodiments) to allow passage of light emitted by the optical fiber 20 therethrough.

Once the tube 12 is properly positioned within the lumen 208 of the body, the optical fiber 20 can be removed from the chamber 12d of the tube 12. A further medical device can then be inserted into the tube so as to perform a specific function or action at the surgical site. For example, the tube and illumination system can be employed during a cardiac catheterization procedure so as to assess heart function and diagnosis cardiac conditions. During this procedure, the tube or catheter 12 is inserted into a vein in the arm, neck or groin of the patient, and then the tube, with the assistance of the illumination system can be passed through the body to a selected site or location in the heart. The illumination system can be used to generate and emit light in the red light range so as to assist the doctor in determining the location of the catheter in the human body.

According to another practice, the tube 12 and the illumination system can be used as part of an angiography or arteriography procedure. During the angiography procedure, the tube or catheter 12 can be inserted into a lumen, such as vein or artery (e.g., femoral artery) of the patient, and the illumination system (e.g., light source 22 and optical fiber 20) helps emit light within the artery to transilluminate the artery and surrounding tissue. The light can help the doctor locate or thread the tube to the proper location within the heart. Once the tube is properly located, the optical fiber can be removed from the tube. The angiography procedure can be used to help visualize the inside, or lumen, of blood vessels and organs of the body, with particular interest in the arteries, veins, and the heart chambers. This is traditionally done by injecting a radio-opaque contrast agent into the blood vessel and imaging using X-ray based techniques such as fluoroscopy.

According to still another practice, the illumination system can be used to assist in angioplasty procedures. For example, the tube or catheter 12 can be inserted within a vein and the optical fiber 20 can be inserted within the tube. The illumination system via the optical fiber 20 emits light at the distal end of the tube to help locate the tube within the body. Once the tube is properly positioned, the optical fiber can be removed from the tube. Angioplasty is a minimally invasive, endovascular procedure to widen narrowed or obstructed arteries or veins, typically to treat arterial atherosclerosis. A deflated balloon attached to a catheter (e.g., a balloon catheter) is passed over a guide-wire into the narrowed vessel and then inflated to a fixed size. The balloon forces expansion of the blood vessel and the surrounding muscular wall, allowing an improved blood flow. A structural support, such as a stent, can then be inserted at the time of ballooning to ensure the vessel remains open, and the balloon is then deflated and withdrawn.

Figure 12:
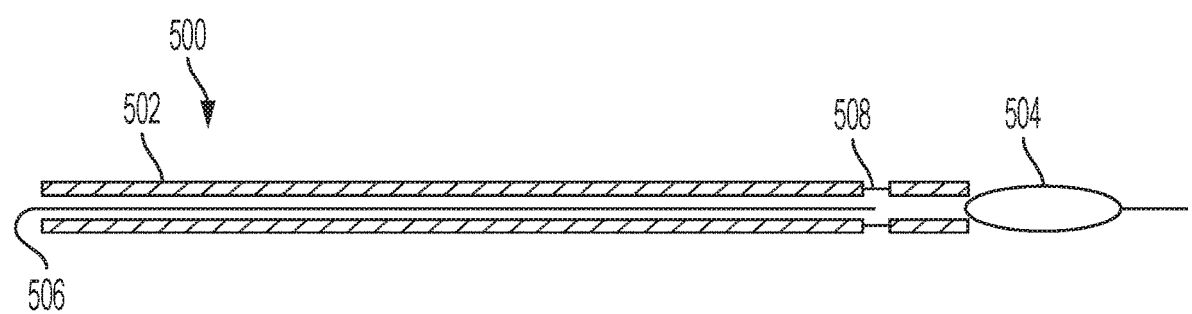
FIG. 12 is a schematic depiction of the illumination system of the present invention according to an embodiment for performing angioplasty.

By way of further illustration, FIG. 12 schematically depicts a system 500 according to an embodiment for performing angioplasty. The system 500 includes a tube (e.g., a catheter) 502, which extends from a proximal end to a distal end. At the distal end of the tube, an inflatable balloon 504 is attached that can be transitioned from a deflated state into an inflated state using the techniques well known in the art. An optical fiber 506 is disposed within the lumen of the tube and receives light from a light source (not shown). At least a portion of the light received by the optical fiber exits via its distal end and passes through a transparent window 508 of the catheter and through the tissue to be observed externally so as to allow a practitioner to position the balloon in proximity of a blockage, e.g., an arterial blockage. As noted above, the inflation of the balloon helps expand the atrial passage and improve the blood flow.

Those having ordinary skill in the art will appreciate that various changes can be made to the above embodiments without departing from the scope of the invention.

What is claimed is:

1. A nasogastric system comprising:
   a light source configured to generate light with a wavelength in a range of about 600 nm to about 700 nm,
   a nasogastric feeding tube configured for placement within a gastrointestinal tract for administration of any of enteral nutrition and medicine to a subject,
   wherein the tube includes:
      a proximal end,
      a distal end, and
      a side wall extending from the proximal end to the distal end, said side wall including a plurality of openings through which any of said enteral nutrition and medicine introduced into the tube via its proximal end can be administered to the subject, and said side wall having at least one portion that is substantially transparent to the light generated by the light source; and
   an optical fiber having a proximal end optically coupled to the light source for receiving at least a portion of the light emitted by the light source and a distal end through which light exits the optical fiber,
      wherein the optical fiber is removably positioned in a lumen of the tube such that at least a portion of the light emitted by the optical fiber can pass through said substantially transparent portion of the side wall of the tube to be detected external to the subject's body.

2. The system of claim 1, wherein the at least a portion of the light exiting the optical fiber through the distal end has a dispersed pattern.

3. The system of claim 1, wherein the optical fiber includes at least one light-emitting segment for emitting light received from the light source, wherein the light-emitting segment is disposed in registration with the distal end of the tube.

4. The system of claim 1, wherein the optical fiber includes a plurality of light-emitting segments for emitting light received from the light source, wherein each of the light-emitting segments is disposed in registration with the distal end of the tube.

5. The system of claim 1, wherein the optical fiber comprises at least one light-emitting segment positioned so as to allow for side emission of light exiting therefrom.

6. The system of claim 1, wherein the optical fiber comprises at least one light-emitting segment positioned so as to allow for axial emission of light from a distal end thereof.

7. The system of claim 1, wherein a distal end of the optical fiber is bent so as to direct light emitted therefrom to the at least one of the openings in the tube.

8. The system of claim 1, wherein the side wall of the tube is substantially transparent to light emitted by the optical fiber.

9. The system of claim 1, wherein the tube is composed of any of silicone rubber, polyurethane or polyethylene.

10. The system of claim 1, wherein the light source comprises a source of visible light.

11. The system of claim 10, wherein the visible light is substantially monochromatic.

12. The system of claim 1, wherein the light source comprises a source of infrared radiation.

13. The system of claim 1, wherein the light source comprises a light emitting diode (LED) or a laser diode.

14. The system of claim 1, wherein the light emitted at the distal end of the tube transilluminates the gastrointestinal tract and surrounding tissue so as to be able to visually locate the distal end of the tube within the gastrointestinal tract.

15. The system of claim 1, further comprising a lens for coupling light from the light source to the optical fiber.

16. The system of claim 1, wherein the optical fiber is a single mode fiber or a multi-mode fiber.

17. The system of claim 1, wherein the optical fiber has a diameter in a range of between about 0.5 mm and about 2 mm.

18. The system of claim 1, further comprising a detector for detecting the light after passage through the tissue of a subject.

19. The system of claim 18, wherein the detector comprises a camera or an infrared detector.

20. The system of claim 1, wherein the at least one opening provides a passageway between the lumen of the tube and the gastrointestinal tract.

21. The system of claim 1, wherein the visible light is red light.

* * * * *